US006463117B1

(12) United States Patent
Hsieh

(10) Patent No.: US 6,463,117 B1
(45) Date of Patent: Oct. 8, 2002

(54) METHODS AND APPARATUS FOR TILTED HELICAL IMAGE RECONSTRUCTION IN CT IMAGING

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/718,916

(22) Filed: Nov. 22, 2000

(51) Int. Cl.$^7$ ................................................ A61B 6/03
(52) U.S. Cl. ............................ 378/15; 378/19; 378/901
(58) Field of Search ............................... 378/4, 15, 20, 378/901, 205, 19

(56) References Cited

U.S. PATENT DOCUMENTS

| | | | | |
|---|---|---|---|---|
| 5,408,511 A | * | 4/1995 | Grangeat et al. | 378/19 |
| 5,457,724 A | * | 10/1995 | Toth | 378/4 |
| 5,841,830 A | * | 11/1998 | Barni et al. | 378/15 |
| 6,061,420 A | * | 5/2000 | Strong et al. | 378/4 |
| 6,229,869 B1 | * | 5/2001 | Hu | 378/4 |

* cited by examiner

Primary Examiner—Drew A. Dunn
(74) Attorney, Agent, or Firm—Carl B. Horton, Esq.; Armstrong Teasdale LLP

(57) ABSTRACT

To reduce the computational load in comparison to the iso-center shift described above, instead of selecting the z-axis of the coordinate system as the iso-center for reconstruction, the gantry iso-center of one of the detector rows (e.g., one of the center rows) is selected as the reconstruction iso-center. In this arrangement, the detector row for which the iso-center is based need not to undergo protection shift, since the defined reconstruction iso-center is the row iso-center. Data from the other detector rows is shifted relative to the selected detector row. When the gantry iso-center of one of the detector rows (e.g., one of the center rows) is selected as the reconstruction iso-center, the reconstructed image will be shifted along y'-axis relative to the original compensation schemes described above. To ensure the images generated with both schemes are identical in location, an adjustment can be added in the backprojection process.

13 Claims, 2 Drawing Sheets

METHODS AND APPARATUS FOR TILTED HELICAL IMAGE RECONSTRUCTION IN CT IMAGING

BACKGROUND OF THE INVENTION

This invention relates generally to methods and apparatus for generating images from data collected in a CT scan, and more particularly to generating images from data collected in a helical scan with a gantry tilted.

In at least some computed tomography (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent the scintillator.

In some clinical applications, a helical CT scan is performed with the gantry tilted. For example, when performing head scans, the CT gantry is tilted to avoid radiation to the eyes. For multi-slice helical CT, however, image artifacts will result if the projection data is not properly adjusted. For example, in multislice CT, the iso-centers defined by the gantry do not align with the image reconstruction iso-center. To avoid image artifacts, the projection data is shifted so that the gantry iso-centers coincides with the reconstruction iso-center. The amount of shift depends on the tilt angle, detector row, and the projection angle. The adjustment process is complex and requires significant computation.

BRIEF SUMMARY OF THE INVENTION

To reduce the computational load in comparison to the iso-center shift described above, instead of selecting the z-axis of the coordinate system as the iso-center for reconstruction, the gantry iso-center of one of the detector rows (e.g., one of the center rows) is selected as the reconstruction iso-center. In this arrangement, the detector row for which the iso-center is based need not to undergo iso-center shift, since the defined reconstruction iso-center is the row iso-center. Data from the other detector rows is shifted relative to the selected detector row.

When the gantry iso-center of one of the detector rows (e.g., one of the center rows) is selected as the reconstruction iso-center, the reconstructed image will be shifted along y'-axis relative to the original compensation schemes described above. To ensure the images generated with both schemes are identical in location, an adjustment can be added in the backprojection process.

By selecting the gantry iso-center of one of the detector rows (e.g., one of the center rows) as the reconstruction iso-center as described above, and in a four row detector, only data collected from 3 out of the 4 detector rows need be shifted, which represents a 25% saving in terms of computation for the iso-center shift. For a twin scanner configuration (i.e., a detector with 2 rows of detector cells), a 50% saving in terms of computation can be realized.

DETAILED DESCRIPTION OF THE INVENTION

Figure 1:
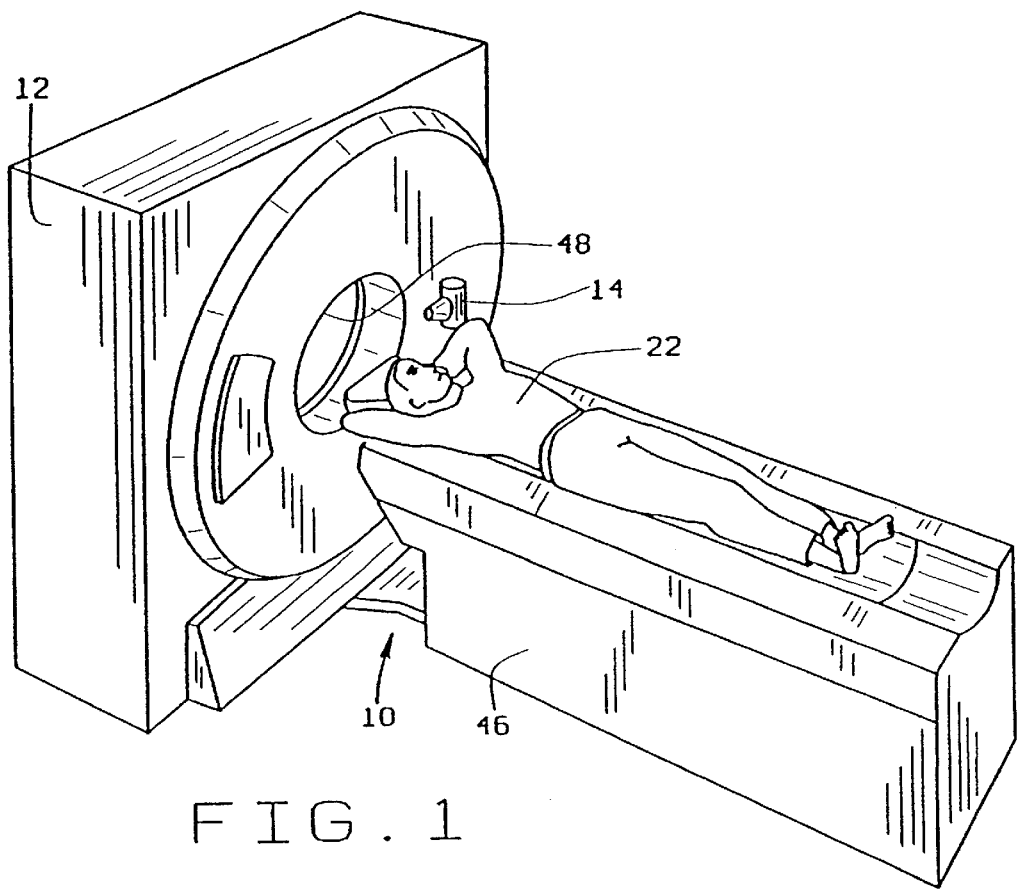
FIG. 1 is a pictorial view of a CT imaging system.
Figure 2:
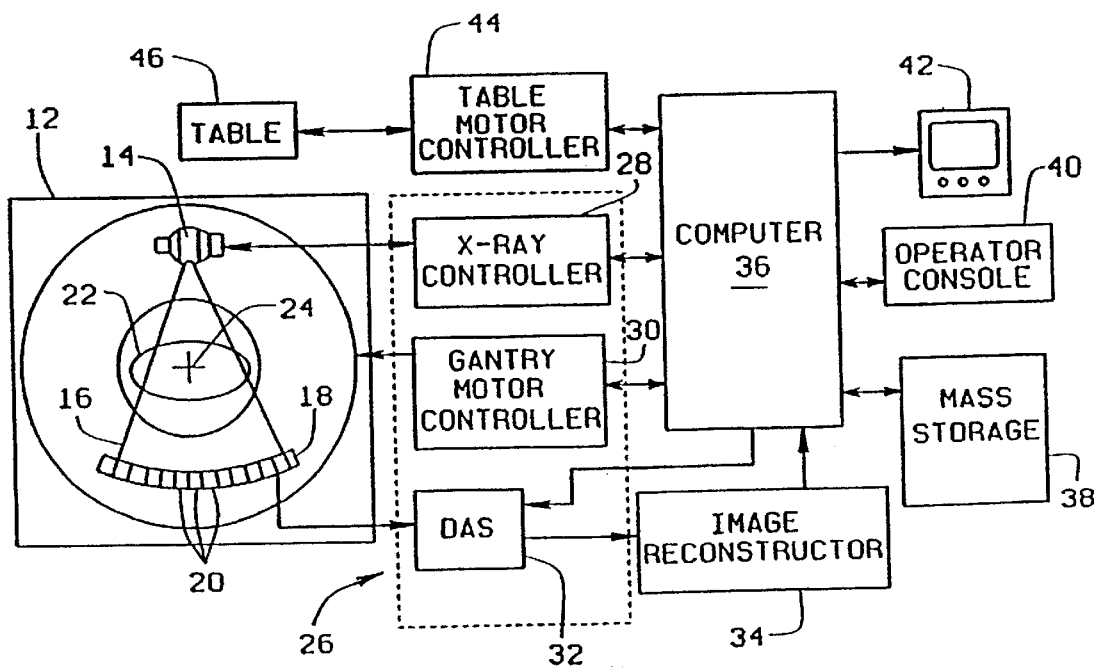
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
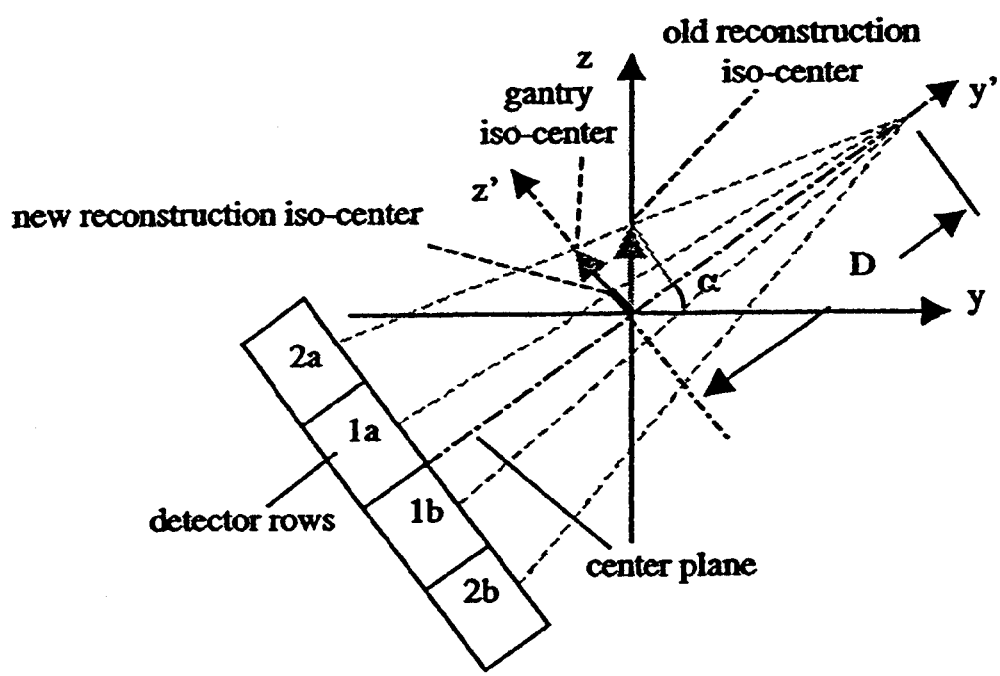
FIG. 3 is schematic illustration of misalignment between a gantry iso-center and a reconstruction iso-center.

FIG. 3 is schematic illustration of misalignment between a gantry iso-center and a reconstruction iso-center. If the angular difference in the detector row plane between two rays that pass from x-ray source through two iso-centers is denoted by ψ, the following relationship exists:

$$\psi = \tan^{-1}\left(\frac{rt \cdot \tan\alpha \cdot \sin\beta}{D + rt \cdot \tan\alpha - rt \cdot \tan\alpha \cdot \cos\beta}\right) \quad (1)$$

In this equation, r=1 or −1, depending on the patient table moving toward or away from the gantry, t is the distance of the gantry iso-center for each row to the origin of the coordinate system. β is the projection angle, D is the source to iso-center distance, and α is the gantry tilt angle.

FIG. 3 illustrates the distance of the gantry iso-center t for detector row 2a. If the detector aperture is q mm, the corresponding t values are −1.5q, −05.q, 0.5q, and 1.5q, for detector rows 2a, 1a, 1b, and 2b of a four-row detector CT. In the image reconstruction process, each row therefore needs to be shifted for every view. Performing such iso-center shift is computationally expensive.

Such adjustment, or shifting, can be performed by a processor in image reconstructor 34. Reconstructor 34 includes, for example, a memory coupled to the processor for storing a designation of one detector row as an iso-center for image reconstruction. Reconstructor 34 also includes a processor for adjusting the data collected based on the selected image reconstruction iso-center.

In accordance with one embodiment of the present invention, and to reduce the computational load in comparison to the iso-center shift described above, instead of selecting the z-axis of the coordinate system as the iso-center for reconstruction, the gantry iso-center of one of the detector rows (e.g., one of the center rows) is selected as the reconstruction iso-center. In this arrangement, the detector row for which the iso-center is based need not to undergo iso-center shift, since the defined reconstruction iso-center is the row iso-center. Data from the other detector rows is shifted relative to the selected detector row.

For example, and referring to FIG. 3, if row 1a is selected as the reference row for the reconstruction iso-center, the shifting formula set forth above in Equation 1 still holds. However, the t values are now −1.0q, 0.0q, 1.0q, and 2.0q, respectively for the four rows. 0.0q means no shift for row 1a. Therefore, only data collected from 3 out of the 4 detector rows need be shifted, which represents a 25% saving in terms of computation for the iso-center shift. For a twin scanner configuration (i.e., a detector with 2 rows of detector cells), a 50% saving in terms of computation can be realized.

In addition, because the data collected from detector row 1a is not shifted, the high-frequency contents in the original signal are better preserved. Preserving the high-frequency contents of the original signal is especially beneficial if spatial domain interpolation techniques are utilized in which the frequency contents of the original signal are not well preserved.

When the gantry iso-center of one of the detector rows (e.g., one of the center rows) is selected as the reconstruction iso-center, the reconstructed image will be shifted along y'-axis relative to the original compensation schemes described above. To ensure the images generated with both schemes are identical in location, an adjustment can be added in the backprojection process. That is, reconstructed images are to be centered at $(c_x, c_y+\Delta)$, where $$\Delta = rt_n \tan(\alpha) \quad (2)$$

In this equation, $t_n$ represents the distance of the iso-center for detector row n to the origin of the coordinate system. For the example given above, $t_n$=−0.5q. $(c_x, c_y)$ represents the reconstructed image center of the original compensation scheme.

While the invention has been described in terms of various specific embodiments, those skilled in the art will recognize that the invention can be practiced with modification within the spirit and scope of the claims.

What is claimed is:

1. A method for adjusting data collected in a CT scan using a CT imaging system, the system including a gantry having secured thereto a detector with a plurality of detector rows, the gantry being tilted at an angle during the scan, said method comprising the steps of:

selecting one of the detector rows as an iso-center for image reconstruction; and adjusting the data collected from the other detector rows based on the selected image reconstruction iso-center.

2. A method in accordance with claim 1 wherein the detector comprises four detector rows.

3. A method in accordance with claim 2 wherein one of the inner two detector rows is the selected image reconstruction iso-center.

4. A method in accordance with claim 1 wherein the detector comprises two detector rows.

5. A method in accordance with claim 1 further comprising the step of centering an image reconstructed using the adjusted center at $(c_x, c_y+\Delta)$, where $$\Delta = rt_n \tan(\alpha),$$

where $t_n$ represents the distance of the iso-center for detector row n to an origin of the coordinate system.

6. A processor programmed to adjust data collected in a CT scan using a CT imaging system, the system including a gantry having secured thereto a detector with a plurality of detector rows, the gantry being tilted at an angle during the scan, said processor programmed to:

adjust data collected during the scan based on one of the detector rows as the image reconstruction iso-center; and center an image reconstructed using the adjusted center at $(c_x, c_y+\Delta)$, where $$\Delta = rt_n \tan(\alpha),$$

where $t_n$ represents the distance of the iso-center for detector row n to an origin of the coordinate system.

7. A processor in accordance with claim 6 wherein the detector comprises four detector rows, and wherein one of the inner two detector rows is the selected image reconstruction iso-center.

8. A processor in accordance with claim 6 wherein the detector comprises two detector rows.

9. Apparatus for adjusting data collected in a CT scan using a CT imaging system, the system including a gantry having secured thereto a detector with a plurality of detector rows, the gantry being tilted at an angle during the scan, said apparatus comprising:

means for storing a designation of one detector row as an iso-center for image reconstruction; and means for adjusting the data collected from the other detector rows based on the selected image reconstruction iso-center.

10. Apparatus in accordance with claim 9 wherein the detector comprises four detector rows.

11. Apparatus in accordance with claim 10 wherein one of the inner two detector rows is the selected image reconstruction iso-center.

12. Apparatus in accordance with claim 9 wherein the detector comprises two detector rows.

13. Apparatus in accordance with claim 9 further comprising means for centering an image reconstructed using the adjusted center at $(c_x, c_y+\Delta)$, where $$\Delta = rt_n \tan(\alpha),$$

where $t_n$ represents the distance of the iso-center for detector row n to an origin of the coordinate system.

* * * * *